United States Patent [19]

Denis et al.

[11] Patent Number: 5,198,577
[45] Date of Patent: Mar. 30, 1993

[54] PREPARATION OF ADIPIC ACID BY HYDROCARBONYLATION OF PENTENIC ACIDS

[75] Inventors: Philippe Denis, Decines; Jean-Michel Grosselin, Francheville, both of France

[73] Assignee: Rhone-Poulenc Chimie, Courbevoie, France

[21] Appl. No.: 761,459

[22] Filed: Sep. 18, 1991

[30] Foreign Application Priority Data

Sep. 18, 1990 [FR] France ................... 90 11714

[51] Int. Cl.$^5$ ............................................. C07C 51/14
[52] U.S. Cl. ................................................. 562/522
[58] Field of Search ..................................... 562/522

[56] References Cited

U.S. PATENT DOCUMENTS 3,579,552  5/1971  Craddock et al. ............ 260/413
4,788,333  11/1988  Burke ........................... 260/413
4,788,334  11/1988  Burke ........................... 562/522

FOREIGN PATENT DOCUMENTS 2015735  4/1970  European Pat. Off. .
0274076  7/1988  European Pat. Off. .

Primary Examiner—Arthur C. Prescott
Attorney, Agent, or Firm—Burns, Doane, Swecker & Mathis

[57] ABSTRACT

Adipic acid is selectively prepared, in good yields, by reacting at least one pentenic acid with water and carbon monoxide, the partial pressure of which, measured at 25° C., being less than or equal to 20 bar, in the presence of a catalytically effective amount of a rhodium-based catalyst and at least one iodine-containing promoter therefor, at a temperature ranging from 100° to 240° C. and at superatmospheric pressure, and in a liquid reaction medium which comprises a saturated aliphatic or aromatic carboxylic acid having up to 20 carbon atoms.

10 Claims, No Drawings

PREPARATION OF ADIPIC ACID BY HYDROCARBONYLATION OF PENTENIC ACIDS

CROSS-REFERENCE TO COMPANION APPLICATION

Our copending application Ser. No. 761,497, filed concurrently herewith and assigned to the assignee hereof.

BACKGROUND OF THE INVENTION

1. Field of the invention

The present invention relates to the preparation of adipic acid by hydrocarboxylation to pentenic acids and, more especially, to the preparation of adipic acid by reacting water and carbon monoxide with at least one pentenic acid, in the presence of a rhodium-based catalyst and of at least one iodine-containing promoter therefor.

2. Description of the Prior Art

Published European Patent Application No. 188,209 describes a process for the preparation of linear dicarboxylic acids, in particular adipic acid, by reacting unsaturated monocarboxylic acids, in particular 3-pentenoic acid, with carbon monoxide and water in the presence of a rhodium-based catalyst and an iodine-containing promoter, the reaction being conducted in a solvent such as methylene chloride at a temperature of 100° to 240° C. and under a total pressure of from 14 to 240 atm; a temperature of from 150° to 180° C. and a total pressure of from 24 to 40 atmospheres are considered to be preferable. The partial pressure of carbon monoxide typically ranges from 10 to 35 atm and preferably from 10 to 17 atm. The selection of the solvent is considered to be critical according to such '209 application and it too is considered that solvents such as acetic acid are undesirable because of the low degrees of linearity of the final products obtained in their presence.

Similarly, it too is noted that nonpolar solvents such as cyclohexane and toluene are themselves also undesirable because of their propensity to promote directly the formation of branched final products and, indirectly, saturated monocarboxylic acids.

Published European Patent Application No. 0,274,076 describes a process for the preparation of linear carboxylic acids by hydroxycarboxylation of unsaturated esters or of terminally unsaturated alkenes having from 4 to 16 carbon atoms in the presence of a rhodium-based catalyst and an iodine-containing promoter therefor. The reaction is conducted in a solvent selected from among methylene chloride, 1,2-dichloroethane and aromatic solvents, such selection being of no consequence, and an aliphatic or aromatic acid having a pKa ranging from 4.2 to 5.2 is present as a reaction accelerator. The partial pressure of the carbon monoxide ranges from 10 to 200 and preferably from 13 to 20 atm.

However, when employing pentenic ester starting materials, the formation of methyl monoadipate is characteristic thereof.

SUMMARY OF THE INVENTION

Accordingly, a major object of the present invention is the provision of an improved process for the selective production of adipic acid by hydrocarboxylation of pentenic acids in the presence of a rhodium-based catalyst and an iodine-containing promoter therefor, in a carboxylic acid solvent.

Briefly, the present invention features a process for the preparation of adipic acid, comprising reacting water and carbon monoxide with at least one pentenic acid, in the presence of a catalytically effective amount of a rhodium-based catalyst and of at least one iodine-containing promoter therefor, at a temperature ranging from 100° to 240° C., at a pressure which is greater than atmospheric pressure, and further wherein:

(a) the reaction is carried out in a reaction medium comprising a saturated aliphatic or aromatic carboxylic acid having not more than 20 carbon atoms, and (b) the partial pressure of the carbon monoxide, measured at 25° C., is less than or equal to 20 bar.

DETAILED DESCRIPTION OF THE PREFERRED EMBODIMENTS OF THE INVENTION

More particularly according to the present invention, by the term "pentenic acid" are intended 2-pentenoic acid, 3-pentenoic acid, 4-pentenoic acid and mixtures thereof.

4-Pentenoic acid provides very good results, but is only difficultly available commercially.

3-Pentenoic acid, either alone or mixed with the isomer thereof, is more particularly advantageous, in light of the general availability thereof and the satisfactory results which it provides per the process of the invention.

The process according to the present invention requires the presence of a rhodium-based catalyst. Any rhodium source is suitable for this purpose.

Exemplary rhodium sources suitable for carrying out the process of the invention include:

Rh metal; $Rh_2O_3$;
$RhCl_3$; $RhCl_3.3H_2O$;
$RhBr_3$; $RhBr_3.3H_2O$;
$RhI_3$; $Rh(NO_3)_3$; $Rh(NO_3)_3.2H_2O$;
$Rh_2(CO)_4Cl_2$; $Rh_2(CO)_4Br_2$; $Rh_2(CO)_4I_2$;
$Rh(CO)Cl[P(C_6H_5)_3]_2$;
$Rh[P(C_6H_5)_3]_3]_2(CO)I$;
$Rh[P(C_6H_5)_3]_3Br$;
$Rh_4(CO)_{12}$; $Rh_6(CO)_{16}$; $Rh(CO)_2(acac)$;
$Rh(Cod)(acac)_2$; $Rh(acac)_3$;
$Rh_2(Cod)_2Cl_2.Rh_2(CO_2CH_3)_4$;
$HRh(CO)[P(C_6H_5)_3]_3$;

(Cod = 1,5-cyclooctadiene; acac = acetylacetonate)

The following rhodium sources are more particularly preferred for carrying out the process of the invention:

$HRh(CO)[P(C_6H_5)_3]_3$;
$Rh(CO)Cl[P(C_6H_5)_3]_2$;
$Rh_2(Cod)_2Cl_2$;
$Rh_2(CO)_4Cl_2$;
$RhI_3$; $RhCl_3.3H_2O$; $Rh(acac)_3$;
$Rh(Cod)(acac)_2$; $Rh_2(CO_2CH_3)_4$; $Rh_4(CO)_{12}$; and $Rh_6(CO)_{16}$.

The quantity of rhodium to be used may vary over wide limits.

In general, a quantity ranging from $10^{-3}$ to $10^{-1}$, expressed in moles of metallic rhodium per liter of reaction mixture, provides satisfactory results. Smaller quantities can be used; however, it is found that the reaction rate is low. The only disadvantages of larger quantities are those of economy.

The concentration of rhodium preferably ranges from $5 \times 10^{-3}$ to $10^{-2}$ (inclusive) mol/l.

By "iodine-containing promoter" according to the present invention are intended HI and organoiodine compounds capable of generating HI under the conditions of reaction and, in particular, $C_1$–$C_{10}$ alkyl iodides, with methyl iodide being more particularly preferred.

The quantity of the iodine-containing promoter to be used is typically such that the I/Rh molar ratio is greater than or equal to 0.1. It is not desirable that this ratio should exceed 20. The I/Rh molar ratio preferably ranges from 1 to 4, inclusive.

The presence of water is critical and indispensible for conducting the process according to the present invention. The quantity of water to be used is typically such that the water/pentenic acid(s) molar ratio ranges from 1 to 10, inclusive.

A smaller quantity presents the disadvantage of limiting the conversion. A larger quantity is not desirable, because of the loss in catalyst activity which is observed.

In an essential characteristic of the present invention, the reaction is carried out in a saturated aliphatic or aromatic carboxylic acid having not more than 20 carbon atoms.

The precise nature of the carboxylic acid is not critical according to the invention, provided that this acid is in the liquid state under the conditions of reaction.

Exemplary such carboxylic acids include acetic acid, propionic acid, butyric acid, valeric acid, adipic acid, benzoic acid and phenylacetic acid.

A $C_1$–$C_4$ aliphatic carboxylic acid is preferably used. Acetic acid is more particularly preferred for carrying out the process of the invention.

The quantity of carboxylic acid which is present in the reaction mixture may vary over wide limits, for example from 10% to 99%, inclusive, by volume of the reaction mixture. This quantity preferably ranges from 30% to 90% by volume, inclusive.

It is another essential characteristic of the process of the invention that the partial pressure of the carbon monoxide, measured at 25° C., be less than or equal to 20 bar.

When the partial pressure of the carbon monoxide, measured at 25° C., is higher than this value, the selectivity in respect of linear and/or branched diacids is very low and the formation of large quantities of 4-methylbutyrolactone, an undesirable compound, is observed.

A minimum partial pressure of 0.5 bar of carbon monoxide (measured at 25° C.) is particularly advantageous.

The partial pressure of carbon monoxide, measured at 25° C., is preferably less than or equal to 10 bar.

The carbon monoxide may be employed substantially pure or of technical grade, as available commercially.

As above indicated, the reaction temperature ranges from 100° to 240° C. Advantageously, the process of the present invention is carried out at a temperature ranging from 160° to 190° C.

The reaction is conducted at a pressure which is higher than atmospheric pressure and, generally, in liquid phase.

The total pressure may vary within certain limits which will depend on the operating technique adopted, on the partial pressure of carbon monoxide and on those of the constituents of the reaction mixture at the selected reaction temperature and, if appropriate, on the autogenous pressure of the pentenic acid(s) present.

The reaction mixture contains the saturated aliphatic or aromatic carboxylic acid, water, one or more rhodium sources, one or more iodine-containing promoters and, if appropriate, all or a portion of the pentenic acids introduced and the reaction products.

Upon completion of the reaction or of the time allocated thereto, the adipic acid is separated off by any suitable means, for example by crystallization and/or distillation of the carboxylic acid.

In order to further illustrate the present invention and the advantages thereof, the following specific examples are given, it being understood that same are intended only as illustrative and in nowise limitative.

EXAMPLE 1

The following materials were introduced into a 125-cm$^3$ stainless steel (Hastelloy B2) autoclave, previously purged with argon:

(i) 325 mg (1.32 mmol) of rhodium in the form of [RhCl(COD)]$_2$;
(ii) 0.64 g (4.5 mmol) of CH$_3$I;
(iii) 2 g (110 mmol) of water;
(iv) 5 g (50 mmol) of 3-pentenoic acid; and
(v) 50 cm$^3$ of acetic acid.

The autoclave was closed hermetically, placed in an agitating oven and connected to the pressurized gas supply. 2 bar of CO were introduced cold and the autoclave was heated to 175° C. in 20 minutes. When this temperature was reached, the pressure was controlled at 8 bar.

After a reaction period of 20 minutes, the CO absorption had ceased; the autoclave was then cooled and degassed.

The reaction solution was analyzed by gas phase chromatography and by high performance liquid chromatography.

The quantities of product formed (molar yield relative to the 3-pentenoic acid charged) were the following:

| Compound | Formula | Yield |
|---|---|---|
| Valeric acid (Pa) | ∼∼COOH | = 1% |
| 4-Pentenoic acid (P4) | ∼∼COOH | = 2.2% |
| 3-Pentenoic acid (P3) | ∼∼COOH | = 13% |
| 2-Pentenoic acid (P2) | ∼∼COOH | = 8.8% |
| 4-Methylbutyrolactone (4ML) | (lactone) | = 8% |
| Ethylsuccinic acid (A3) | HOOC–CH(Et)–CH$_2$–COOH | = 3% |
| Methylglutaric acid (A2) | HOOC–CH$_2$–CH(CH$_3$)–CH$_2$–COOH | = 23% |
| Adipic acid (A1) | HOOC–(CH$_2$)$_4$–COOH | = 54% |

EXAMPLE 2: CONTROL TESTS (A) TO (C)

A first series of tests was carried out in the autoclave and according to the procedure described in Example 1, with only the partial pressure of the carbon monoxide being modified. This pressure (at 175° C.) was equal to the difference between the total pressure ($P_T$) and the autogenous pressure on the order of 4 bar.

The individual conditions and the results obtained, all other conditions being otherwise equal, are reported in Table I below, in which the conventions employed are the same as in Example 1 and t denotes the reaction period at temperature.

TABLE I

| Example | PT bar | t min | DC % | Al % | L % | 4ML % |
|---|---|---|---|---|---|---|
| 1 | 8 | 20 | 87 | 54 | 67 | 8 |
| 2 | 15 | 10 | 100 | 35 | 42 | 10 |
| a | 28 | 20 | " | 22 | 27 | 16 |
| b | 60 | 15 | " | 18 | 24 | 21 |
| c | 100 | 20 | " | 19 | 27 | 27 |

These results evidence the determining effect of a low partial pressure of CO on the degree of linearity (L) and on the quantity of lactone formed (4 ML).

EXAMPLES 3 TO 5: CONTROL TESTS (D) TO (F)

A second series, similar to the preceding, of tests was carried out in the autoclave and according to the procedure described above, except that the charge contained 50 mmol of 4-pentenoic acid instead of 3-pentenoic acid.

The individual conditions and the results obtained, all other conditions being otherwise equal, are reported in Table II below:

TABLE II

| Example | PT bar | t min | DC % | Al % | L % | 4ML % |
|---|---|---|---|---|---|---|
| 3 | 8 | 20 | 100 | 72 | 78 | 7 |
| 4 | 12 | 10 | " | 65 | 73 | 10 |
| 5 | 15 | 20 | " | 42 | 51 | 15 |
| d | 28 | 15 | " | 48 | 59 | 17 |
| e | 50 | 20 | " | 43 | 53 | 17 |
| f | 100 | 20 | " | 40 | 56 | 29 |

EXAMPLE 6 CONTROL TESTS (G) AND (H)

A third series of tests similar to the first series was carried out in the autoclave and according to the procedure described above, except that the charge contained 50 mmol of 4-pentenoic acid instead of 3-pentenoic acid and a quantity of methyl iodide which was halved.

The individual conditions and the results obtained, all other conditions being otherwise equal, are reported in Table III below:

TABLE III

| Example | PT bar | t min | DC % | AL % | L % | 4ML % |
|---|---|---|---|---|---|---|
| 6 | 8 | 20 | 100 | 71 | 80 | 8 |
| g | 50 | 20 | " | 43 | 60 | 26 |
| h | 100 | 35 | " | 36 | 58 | 36 |

EXAMPLES 7 AND 8: CONTROL TESTS (I) AND (J)

A fourth series of tests was carried out in the autoclave and according to the procedure described in Examples 1 and 2, except that 50 mmol of 2-pentenoic acid were employed instead of 3-pentenoic acid.

The individual conditions and the results obtained, all other conditions being otherwise equal, are reported in Table IV below:

TABLE IV

| Example | PT bar | t min | DC % | Al % | L % | 4ML % |
|---|---|---|---|---|---|---|
| 7 | 8 | 40 | 35 | 23.5 | 55 | 4 |
| 8 | 12 | 90 | 77 | 27 | 49 | 7 |
| i | 28 | 100 | 98 | 17 | 30 | 6.5 |
| j | 50 | 120 | 97 | 16 | 28 | 7 |

The presence of large quantities ($\approx$35-45%) of valeric acid was noted in this series of tests; in all of the preceding tests this saturated acid, when present, represented only $\approx$0.5 to 2%.

EXAMPLE 9

A test was carried out in the autoclave and according to the procedure described above, on a charge consisting of:
(i) 25 mmol of 3-pentenoic acid;
(ii) 110 mmol of water;
(iii) 1.32 mmol of rhodium in the form of [RhCl(COD)]$_2$;
(iv) 2.6 mmol of methyl iodide; and
(v) 50 cm$^3$ of acetic acid.

The results obtained after 30 minutes of reaction at 175° C. at a total pressure of 8 bar were the following:
(a) DC=100%
(b) Al=58%
(c) L=67%
(d) 4ML=6%

EXAMPLE 10

The procedure of Example 9 above was repeated, except that the charge contained 100 mmol of 3-pentenoic acid.

The results obtained after 80 minutes of reaction, all other conditions being otherwise equal, were the following:
(a) DC=99%
(b) Al=58%
(c) L=68%
(d) 4ML=6%

EXAMPLES 11 to 15

A fifth series of tests was carried out in the autoclave and according to the procedure described above, on a charge containing:
(i) 1.32 mmol of rhodium in the form of [RhCl(COD)]$_2$;
(ii) 2.5 mmol of CH$_3$I;
(iii) 110 mmol of water;
(iv) 50 mmol of 3-pentenoic acid; and
(v) 50 cm$^3$ of acetic acid.

The individual reaction conditions and the results obtained are reported in Table V below:

TABLE V

| Example | T °C. | PT bar | P(CO) bar | t min | DC % | Al % | L % | 4ML % |
|---|---|---|---|---|---|---|---|---|
| 11 | 145 | 8 | 5 | 70 | 100 | 34 | 37 | 5 |
| 12 | 160 | 8 | 4 | 30 | " | 49 | 54 | 5 |
| 13 | 175 | 8 | 3 | 40 | " | 62 | 71 | 6.5 |
| 14 | 190 | 9 | 3 | 20 | 97 | 62 | 76 | 9.5 |
| 15 | 210 | 16 | 6 | 120 | 97 | 35 | 59 | 28 |

In Example 11 an induction period on the order of 40 min was observed before absorption.

In Example 12 an induction period on the order of 20 min was observed before absorption.

EXAMPLES 16 TO 23

A sixth series of tests was carried out under the conditions of Example 13, the quantity of [RhCl(COD)]$_2$ and/or that of CH$_3$I charged being varied.

The individual reaction conditions and the results obtained are reported in Table VI below: (In Example 18, the quantity of water charged was only 10 mmol).

TABLE VI

| Example | Rh mmol | CH$_2$I mmol | I/Rh | t min | DC % | Al % | L % | 4ML % |
|---|---|---|---|---|---|---|---|---|
| 16 | 2.6 | 4.5 | 2 | 40 | 99 | 65 | 78 | 5.6 |
| 17 | " | 2.2 | 1 | 60 | 100 | 65 | 77 | 9.5 |
| 1 | 1.32 | 4.5 | 3.5 | 20 | 87 | 46.5 | 67 | 7 |
| 18 | " | " | " | 120 | 37 | 48 | 68 | 12 |
| 13 | " | 2.25 | 2 | 40 | 100 | 62 | 71 | 6.5 |
| 19 | " | 1.30 | 1 | 180 | 97 | 57 | 73 | 11.5 |
| 20 | " | 0.6 | 0.5 | (24 h) | 80 | 32 | 78 | 29.5 |
| 21 | 0.65 | 1.3 | 2 | 90 | 100 | 55.5 | 65 | 8 |
| 22 | 0.33 | 2.45 | 7.4 | 60 | 99 | 38 | 52 | 17 |
| 23 | 0.33 | 0.6 | 2 | 210 | 88 | 43 | 59 | 8 |

While the invention has been described in terms of various preferred embodiments, the skilled artisan will appreciate that various modifications, substitutions, omissions, and changes may be made without departing from the spirit thereof. Accordingly, it is intended that the scope of the present invention be limited solely by the scope of the following claims, including equivalents thereof.

What is claimed is:

1. A process for the selective preparation of adipic acid, comprising reacting at least one pentenic acid with water and carbon monoxide, the partial pressure of which, measured at 25° C., being less than or equal to 20 bar, in the presence of a catalytically effective amount of a rhodium-based catalyst and at least one iodine-containing promoter therefor, at a temperature ranging from 100° to 240° C. and at super atmospheric pressure, and in a liquid reaction medium which comprises a saturated aliphatic or aromatic carboxylic acid having up to 20 carbon atoms.

2. The process as defined by claim 1, said liquid reaction medium comprising acetic acid.

3. The process as defined by claim 1, said saturated aliphatic or aromatic carboxylic acid comprising at least 10% by volume of said liquid reaction medium.

4. The process as defined by claim 3, said saturated aliphatic or aromatic carboxylic acid comprising from 30% to 90% by volume of said liquid reaction medium.

5. The process as defined by claim 1, the concentration of rhodium values in said liquid reaction medium ranging from $10^{-3}$ to $10^{-1}$ mol/l.

6. The process as defined by claim 1, wherein the I/Rh molar ratio in said liquid reaction medium is at least 0.1.

7. The process as defined by claim 6, said I/Rh molar ratio being no greater than 20.

8. The process as defined by claim 1, wherein the water/pentenic acid(s) molar ratio in said liquid reaction medium ranges from 1 to 10.

9. The process as defined by claim 1, carried out at a temperature ranging from 160° to 190° C.

10. The process as defined by claim 1, the partial pressure of said carbon monoxide, measured at 25° C., being less than or equal to 10 bar.

* * * * *